United States Patent [19]

Akhavi

[11] Patent Number: 4,789,324
[45] Date of Patent: Dec. 6, 1988

[54] MOLDED OPTIC FOR AN INTRAOCULAR LENS

[75] Inventor: David S. Akhavi, Westwood, Calif.

[73] Assignee: Iolab Corporation, Claremont, Calif.

[21] Appl. No.: 943,416

[22] Filed: Dec. 15, 1986

Related U.S. Application Data

[62] Division of Ser. No. 606,807, May 3, 1984, Pat. No. 4,681,953.

[51] Int. Cl.⁴ .............................................. A01J 21/00
[52] U.S. Cl. .................................... 425/352; 425/469; 425/808; 249/122; 249/142; 249/160; 264/1.1
[58] Field of Search ....................... 425/469, 352, 808; 264/1.1, 1.3, 2.2; 249/122, 142, 160–162; 623/6

[56] References Cited

U.S. PATENT DOCUMENTS

| | | | |
|---|---|---|---|
| Re. 31,998 | 10/1985 | Myers | 623/6 |
| 1,717,966 | 6/1929 | Moore | 425/352 |
| 2,253,497 | 8/1941 | Kollmorgan | 425/808 |
| 2,608,344 | 8/1952 | Knocke | 425/809 |
| 3,173,964 | 3/1965 | Mohr | 425/352 |
| 4,540,534 | 9/1985 | Grendol | 425/352 |

FOREIGN PATENT DOCUMENTS 109618  7/1982  Japan ................................. 264/1.3

Primary Examiner—Bernard Nozick
Attorney, Agent, or Firm—Donal B. Tobin

[57] ABSTRACT

An optic for an intraocular lens with finished, molded radii on the anterior and posterior edges of the peripheral surface of the optic. The optic has a thin central optical zone and a surrounding annular ring having sufficient material to support haptics. The ring is thicker than the optical zone and, thus, recesses the posterior surface of the optical zone to provide a capsulotomy space. The present novel optic is produced by novel molding pins which are shaped to provide the finished molded radii on the edges of the optic so that the optic requires little or no post-molding finishing or polishing other than the degating and deflashing.

6 Claims, 6 Drawing Sheets

MOLDED OPTIC FOR AN INTRAOCULAR LENS

This is a division of application Ser. No. 606,807, filed May 3, 1984, now U.S. Pat. No. 4,681,953.

The present invention relates to a molded optic for an intraocular lens, and more particularly to a molded optic with finished radii molded on the edges of the optic which require little or no additional finishing after the molding is completed.

BACKGROUND OF THE INVENTION

It is now commonly accepted that the vision impairing disease known as cataracts can be alleviated by surgically replacing the natural lens of the eye with an artificial intraocular lens.

Intraocular lenses have two principle parts: a medial, light focusing body (also called the optic), made of a non-toxic plastic material which will replace the natural lens of the eye and focus light on the retina, and haptic support portions which extend from the optic to the anatomy of the eye and provide means for fixing and holding the optic in proper position within the eye.

Figure 1:
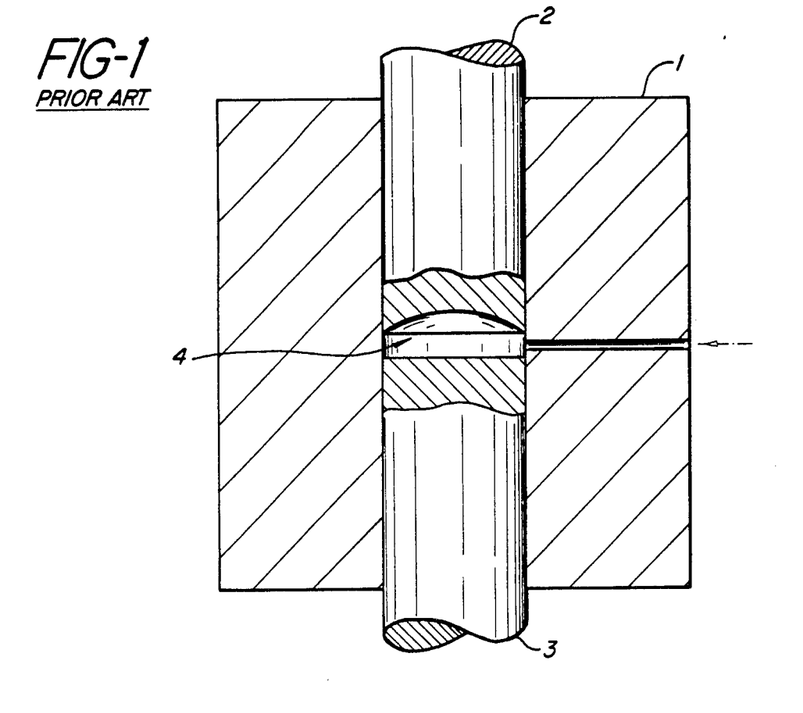
FIG. 1 shows a schematic representation of a mold insert and molding pins of the prior art.

The optics for intraocular lenses are made principally by two processes. Some optics are made by a lathe cutting process whereby cylindrical pieces of plastic are placed on a lathe in an appropriate fixture and the optical surfaces of the optic are cut by conventional lathe cutting techniques. After the cutting is accomplished the edges of the optic may be polished by a variety of polishing practices, including tumbling in an abrasive medium. Although lathe cutting procedures provide satisfactory optical lenses, they are time consuming, labor intensive and therefore, expensive to make. Other intraocular lenses are formed by molding. The molding is accomplished by using a rectangular mold insert, like that shown in FIG. 1, with a cylindrical bore 6 extending through insert 1 from one opposite surface to the other. Molding pins 2 and 3, are inserted into opposite sides of mold insert 1 and into bore 6 and spaced apart at a required distance to provide a molding cavity 4. Molten plastic is directed into molding cavity 4 through a gate in the side of mold insert 1.

Molding pins are made of very hard steel and their confronting surfaces are highly polished to provide good optical quality to the molded optic. In order to polish them properly it is necessary to place the pins in a skirt, like that shown in FIG. 2, and then polish right across the interface between the skirt and the pin. It has previously been found very difficult to place any fine molding detail close to the edge of the pin because of the tendency of the pin to fracture at the edge of the pin.

As a result, the sharp edges of the molded optic have to be removed by subsequent machining and polishing of the edges. Great care must be taken to protect the delicate optical zone of the optic during this final edge finishing.

It would be desirable to mold the optic with finished molded radii at the edges which require only minimum subsequent finishing.

Haptic supports can be formed with a thin filamentary resilient unitary memory retaining plastic fibers, for example polypropylene or some other suitable plastic fibrous material, which is resilient and has good springlike quality so that it may be easily deformed and return to its original shape when the deforming forces are reduced. It has been necessary to make the optic thick enough so holes could be drilled radially into the edge to receive haptic supports. Haptics may be attached to the optic by bonding, gluing, crimping or otherwise fastening the haptic filament into the hole, by a variety of well known processes.

It would be desirable to make the central optical zone of the optic thinner so that the optical properties could be improved and weight of the optic could be reduced but still leave enough material at the edge of the lens to support the haptics.

Figure 1A:
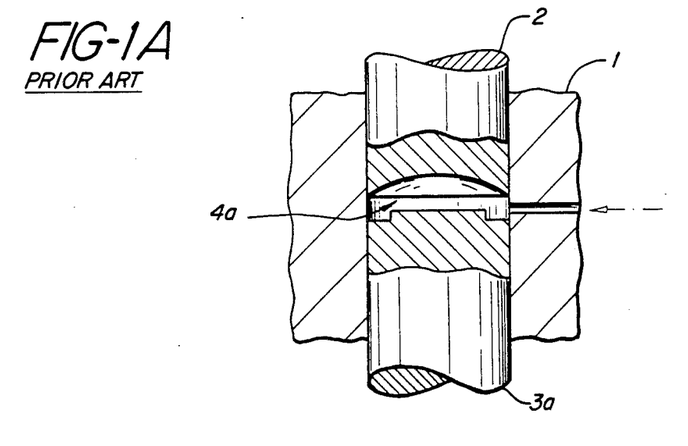

It would also be desirable to space the posterior surface of the optic away from the adjacent anatomy of the eye to provide room to perform a capsulotomy should it be necessary after the lens is inserted in the capsular bag of the eye. The possible need for a capsulotomy is well-known in this art, and its details will not be discussed further in this application. In the past, certain lenses have accomplished this spacing by adding an annular ridge to the posterior surface of the lens. In certain prior art lenses, this ridge has been molded on the back of the optic by machining a groove 7 around the periphery of the posterior pin 3 as shown in FIG. 1a. However, adding a ridge to the back of the optic makes the optic even thicker and still leaves a relatively sharp edge between the edge on the optic which requires further finishing.

It would be desirable to be able to recess part of the posterior surface of the optic at the edge of the optic to support the haptic and at the same time to provide finished molded radii on the edges of the optic which require only minimum subsequent finishing.

SUMMARY OF THE INVENTION

The present invention provides a optic for an intraocular lens with finished, molded radii on the anterior and posterior edges of the peripheral surface of the optic. The present invention also provides a thinner central optical zone and a wide surrounding annular ring having sufficient material to support haptics.

The present invention, which is produced by the novel molding pins and molding process of the present invention, provides a generally circular optic with a circular peripheral surface. A central optical zone having an anterior surface and a posterior surface extends radially outward toward the periphery of the optic. An annular molded plastic ring portion is molded integrally with the central optical zone. The anterior surface of the ring portion conforms to the shape of the anterior surface of the central optical zone and extends to the anterior edge of the peripheral surface of the optic. The anterior edge includes a finished, molded radius one end of which is blended smoothly to the surrounding anterior surface of the ring and the outer end of which blends smoothly to the peripheral edge of the finished optic.

The ring has a posterior surface generally perpendicular to the optical axis of the optic and spaced posteriorly of the posterior surface of the central optical zone. The posterior surface of the ring extends inwardly only to the periphery of the optic zone. The spaced apart posterior surface of the central optical zone and the posterior surface of the ring portion define a recess permitting the posterior surface of the optical zone to be recessed.

The optic has a finished, molded radius on the anterior and posterior peripheral edge of the optic and on the edges of the recess in the back of the optic. These finished, molded radii on the edges of the optic come out of the mold in substantially finished condition so that only a minimum of subsequent finishing is required other than degating and deflashing and finishing is easier.

The novel pins of the present invention are specifically designed to deposit flash and gate material in a controlled area on only a part of the peripheral edge of the optic. The flash area is placed toward the middle of the peripheral edge of the optic so that it can be removed by an easy process of degating and deflashing. It is important that the anterior and posterior edges of the optic be smooth, because these are the parts that are most apt to come in contact with the patient's eye. If there are slight imperfections on the middle of the edge, they are, first, easier to remove and, second, less important because slight imperfections in the middle of the peripheral edge are less apt to come in contact with the interior anatomy of the eye. The present invention leaves only a small amount of flash on the finished, molded radii on the edges of the optic. This flash material may be removed with a single tool. The cutting edge of the tool can be straight and aligned parallel to the optical axis of the optic and hence, parallel to the peripheral edge of the optic. If the finished molded radii have been arranged so that they are tangent to the peripheral edge of the optic, this straight cut will provide a peripheral surface which is tangent to the finished, molded radii on the peripheral edges of the optic.

Alternately, a slight concave curvature may be put into the deflashing tool to provide a slight convex curve to the edge of the optic and a smooth blending with the finished, molded radii on the anterior and posterior peripheral edges of the optic. In the further alternative, the deflashing tool can have a straight central portion with a small concave radii at the edges to blend smoothly with the finished, molded radii on the anterior and posterior peripheral edges of the optic.

The novel pins of the present invention are made by placing a circular groove at a constant radius from the optical axis of the pin and extending 360° around the pin. The anterior pin, which is usually a concave pin to form a convex anterior surface for the molded optic, uses an arcuate groove the inner edge of which blends smoothly with the adjacent concave surface of the anterior pin. The outer edge of the groove is formed so that its tangent is substantially parallel to the axis of the optic and, hence, the optical axis of the molded optic. This outer edge need not be tangent but may be formed at an angle which provides a smooth blend with the peripheral edge of the molded optic. In these instances, a slightly curved deflashing tool would be used for the peripheral edge of the optic. If the tangent to the outer edge of the groove were parallel to the optical axis of the molded optic then the deflashing tool would be flat and also aligned parallel to the optical axis of the optic.

The outer edge of the groove in the anterior pin is spaced a small distance away from the circumference of the anterior pin. A flat surface is provided in the area between the outer edge of the groove in the anterior pin and the circumference of the anterior pin to define a flash area. This flat surface is, preferably, aligned perpendicular to the axis of the pin and, hence, perpendicular to the optical axis of the molded optic.

The posterior pin may have a similar arcuate groove, spaced at a constant radius from the axis of the and running 360° around the posterior pin. The inner edge of the groove blends smoothly with the adjacent surface of the posterior pin. The outer edge of the groove, like the outer edge of the groove in the anterior pin, is aligned so that its tangent is generally parallel to the axis of the pin or, alternatively, is designed to blend smoothly with the adjacent peripheral surface of the optic, after it has been deflashed. The outer edge of the posterior groove is spaced apart from the circumference of the posterior pin. A flat surface, aligned perpendicular to the axis of the posterior pin and, hence, perpendicular to the optical axis of the molded optic, is provided between the outer surface of the posterior groove and the circumference of the posterior pin to define a flash area.

Alternatively, the groove in the posterior pin may be formed as a deep channel to provide an annular ring portion for the optic integrally molded with the optical zone of the optic and to provide a recess in the posterior surface of the optic resulting in a thin, lightweight lens which already has a capsulotomy space provided and thick edges to support the haptics.

When the anterior and posterior pins are placed in the mold insert, in spaced apart fashion to define a molding cavity, the confronting flat surfaces of the respective pins, together with the surrounding cylindrical wall of the bore of the mold insert, will define a generally rectangular flash and gate area through which molten plastic is introduced into the mold cavity. The flash and gate area is placed in the middle of the peripheral edge of the optic and do not extend to the finished, molded radii of the anterior and posterior peripheral edges of the optic.

The grooves in the molding pins may be formed by a variety of processes, including electrical-discharge machining or grinding, or some other suitable process, and then subsequent polishing to provide a pin which will furnish a smooth, finished, molded radius on the edges of the optic.

If a deep channel is required for the posterior pin that deep channel may be made, again, by electrical-discharge machining or by grinding and then subsequent polishing to provide smooth surfaces to form the finished, molded radii for the optic. These grooves are placed in the pins after the optical zone has been shaped and polished into a very high finish. As a result, it is necessary to protect the optical zone of the pins during the subsequent grooving processes by using a masking material such as wax.

These and other features and advantages of the present invention will become more apparent when taken in conjunction with the following detailed description of the preferred embodiments and the following drawings.

BRIEF DESCRIPTION OF THE DRAWINGS

FIGS. 1, 1(A) shows a modification of the prior art molding pins;

DETAILED DESCRIPTION OF THE PREFERRED EMBODIMENT

Figure 2:
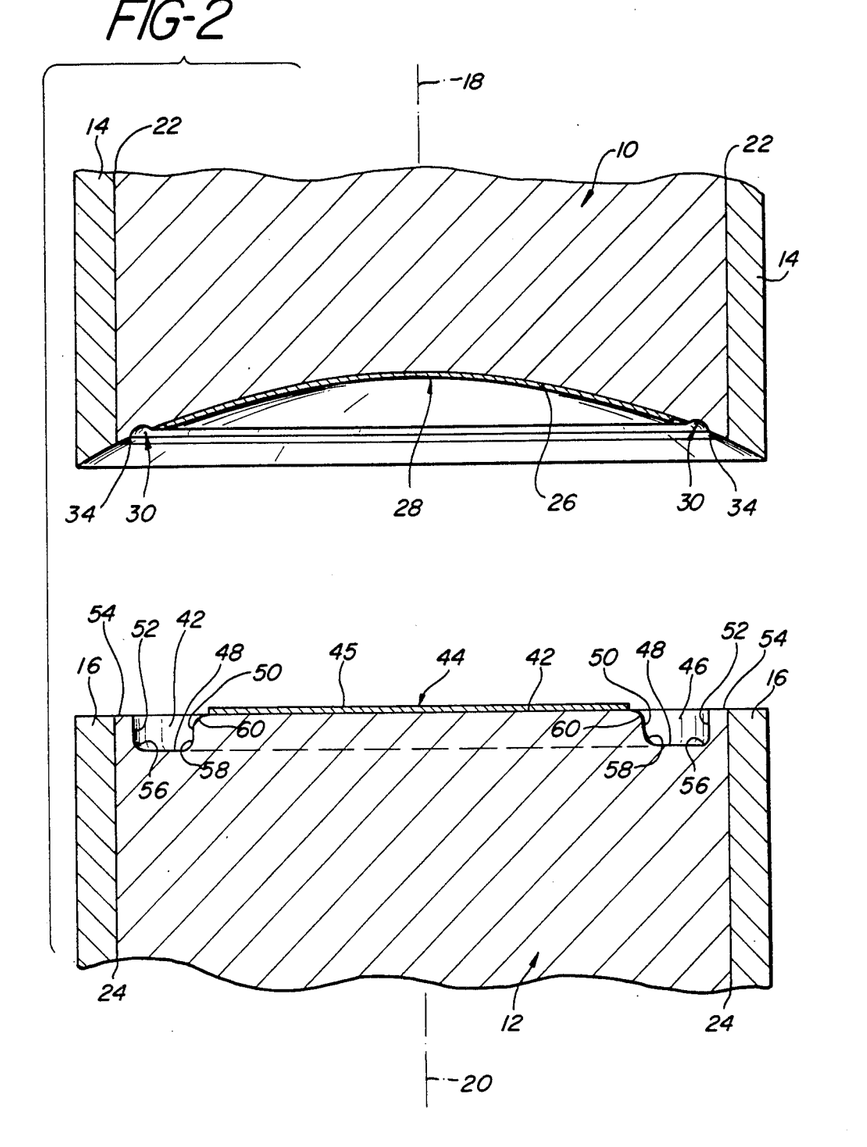
FIG. 2 shows the molding pins of the present invention.

Referring now to FIG. 2 there was shown cross-sectional views of the novel molding pins 10 and 12 of the present invention, respectively, each in its respective machining skirt 14 and 16. For the purposes of this patent application, the molding of a standard plano-convex lens which has a convex anterior surface and a planar posterior surface will be discussed. The present invention is not limited to a plano-convex lens. It can be applied to the full variety of lens configurations that are normally used for intraocular lenses.

Each of molding pins 10 and 12 is a generally cylindrical piece of high strength steel of the kind usually used in molding plastics having axis 18 and 20 and circumferences 22 and 24, respectively.

Pin 10 is the pin used for molding the anterior surface of the optic and will be called the anterior pin. Anterior pin 10 has a concave distal surface 26 having a curvature conforming to the desired optical curvature of the finished optic. This curvature may be a continuous radius or it can be a compound curve, or made in any desired shape. Concave surface 26 of pin 10 is machined and then polished to a highly smooth surface so that the molded optic will provide an optical quality, highly finished surface. Pin 10 is machined and polished in a skirt 14 and the curvature of the lens extends across circumference 22 of pin 10 in a continuous curve. It is necessary to use skirt 14 to support the edges of pin 10 because the high forces experienced during the machining and polishing process could crack or fracture the edge of pin 10. After the distal surface 26 is shaped and polished to the desired optical finish, a protective wax 28 is placed over the central optical zone 27 of distal surface 26 to protect this highly polished central zone during subsequent processing of pin 10.

An annular groove 30 extending at a fixed radius from axis 18 of pin 10, 360° around pin 10 is then placed in a peripheral portion of concave surface 26 of pin 10. Groove 30 is spaced a small distance from the circumference 22 of pin 10. Groove 30 is an arcuate groove defining the curvature intended to be molded into the finished optic. The inner edge 32 of groove 30 blends smoothly with the curvature of adjacent concave surface 26. The outer edge 34 of groove 30 is positioned so that its tangent is generally parallel to axis 18 of pin 10. This tangent need not be exactly parallel to axis 18, but can be at any convenient angle that will provide the desired smooth, finished, molded radius to the optic which is intended to be made by pin 10.

Figure 3:
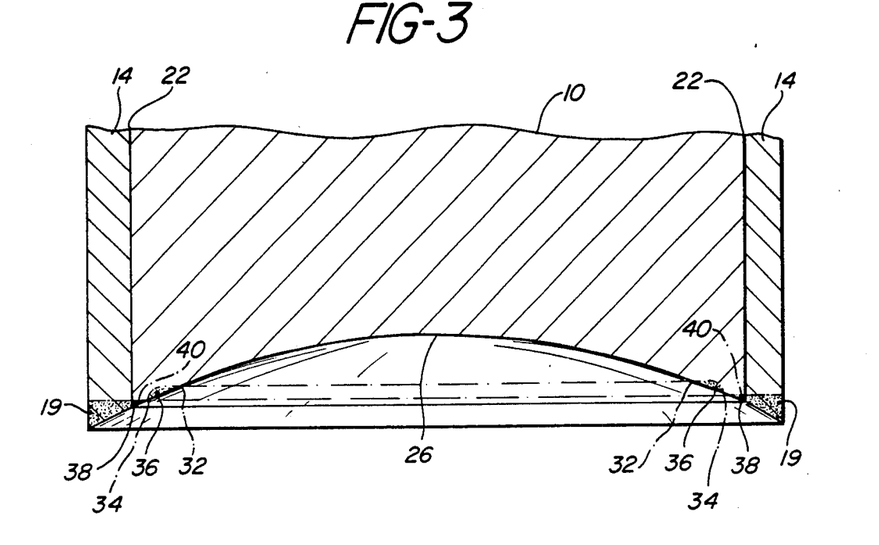
FIGS. 3 and 3(A) show details of the anterior molding pin of the present invention.
Figure 3A:
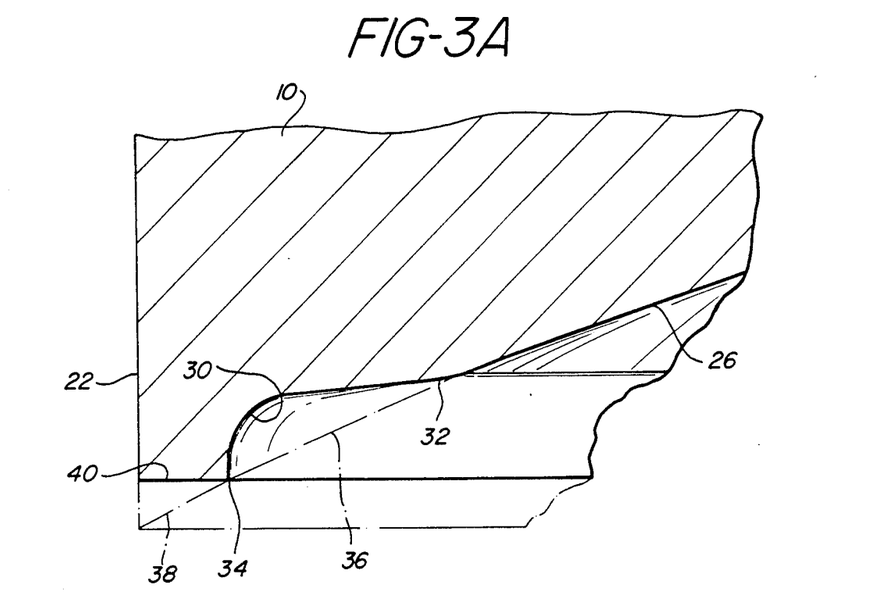

Referring now to FIG. 3 and 3(a) the details of groove 30 and edges 32 and 34 may be seen in greater detail. It can be seen that groove 30 is made by removing the cross-hatched area 36 from concave surface 26 of pin 10. This material may be removed by a variety of processes, but we prefer to use a process known as electrical-discharge machining. This process is described in some detail in Marks Standard Handbook of Mechanical Engineering (8th Ed. 1978) p. 13–71. Electrical-discharge machining is based on the principle of erosion of metal by spark discharge. It is capable of providing very smooth finishes. After area 36 has been remove to form groove 30, material 38 remains between outer edge 34 of groove 30 and circumference 22 of pin 10. Material 38 and adjacent material 19 on skirt 14 is removed by grinding or some other suitable process to form flat end portion 40 on pin 10. Flat 40 is usually aligned perpendicular to the axis of pin 10 but it need not be perpendicular.

Referring again to FIG. 2, the process of forming posterior pin 12 will now be discussed. For the plano convex optic which is being used to illustrate the present invention, distal surface 42 of pin 12 is formed and polished on a flat surface perpendicular to axis 20 of pin 12. After this finishing a polishing operation is completed to form a highly polished optical zone 44 in the central portion of pin 12, optical zone 44 is covered with protective material 45, preferrably wax, so that further processing of pin 12 may be conducted without damaging the highly polished finish an optical zone 44. If it is only desired to process a finished molded radius on the posterior edge of the optic, then a groove is made in the distal surface 42 of pin 12, similar to groove 30 in anterior pin 10. The interior edge of that groove would be blended with the surrounding distal surface 42 of pin 12 and the outer edge of that groove would be formed so that its tangent is substantially parallel to axis 20 of in 12. However, in this preferred embodiment a deep and wide channel 46 is formed in distal surface 42 of pin 12 at a fixed radius from axis 20 of pin 12 running 360° around distal surface 42. Channel 46 can be formed by grinding or electrical-discharge machining or other suitable means. Channel 46 has a base 48, an inner wall 50 and an outer wall 52. Outer wall 52 is spaced a short distance from circumference 24, pin 12, to provide a flat area 54. It can be seen from FIG. 2 that the intersection of base 48 of channel 46 and outer wall 52 form smooth radius 56, the intersection of base 48 and inner wall 50 form smooth radius 58, and the intersection of inner wall 50 and distal surface 42 form smooth radius 60. Smooth radii 56, 58 and 60 provide smooth corners on all of the edges of channel 46.

Figure 4:
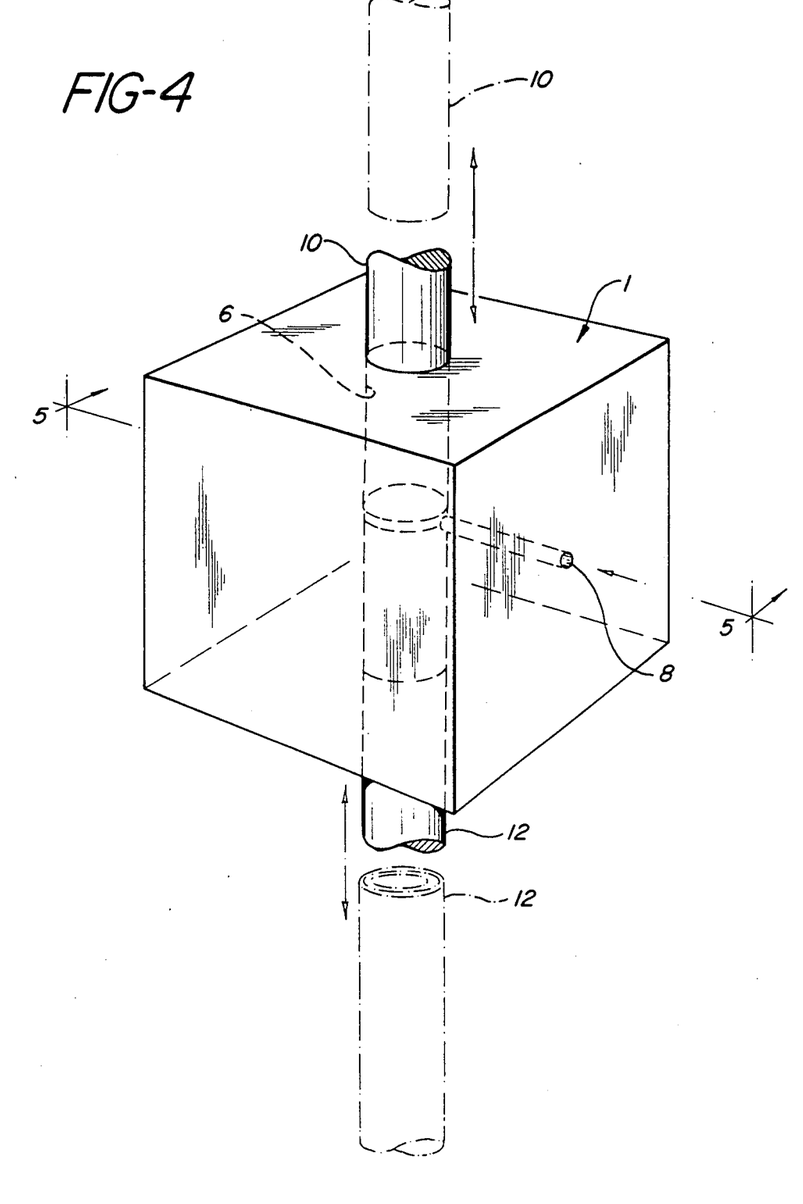
FIG. 4 shows a perspective view of the molding pins of the present invention and the mold insert in which they are used.

Referring now to FIG. 4, pins 10 and 12 may be inserted into bore 6 of mold insert 1 in confronting, spaced apart relationship to form a mold cavity. Access to the mold cavity is provided by molding gate 8, which is a bore drilled transverse to bore 6 in mold insert 1.

Figure 5:
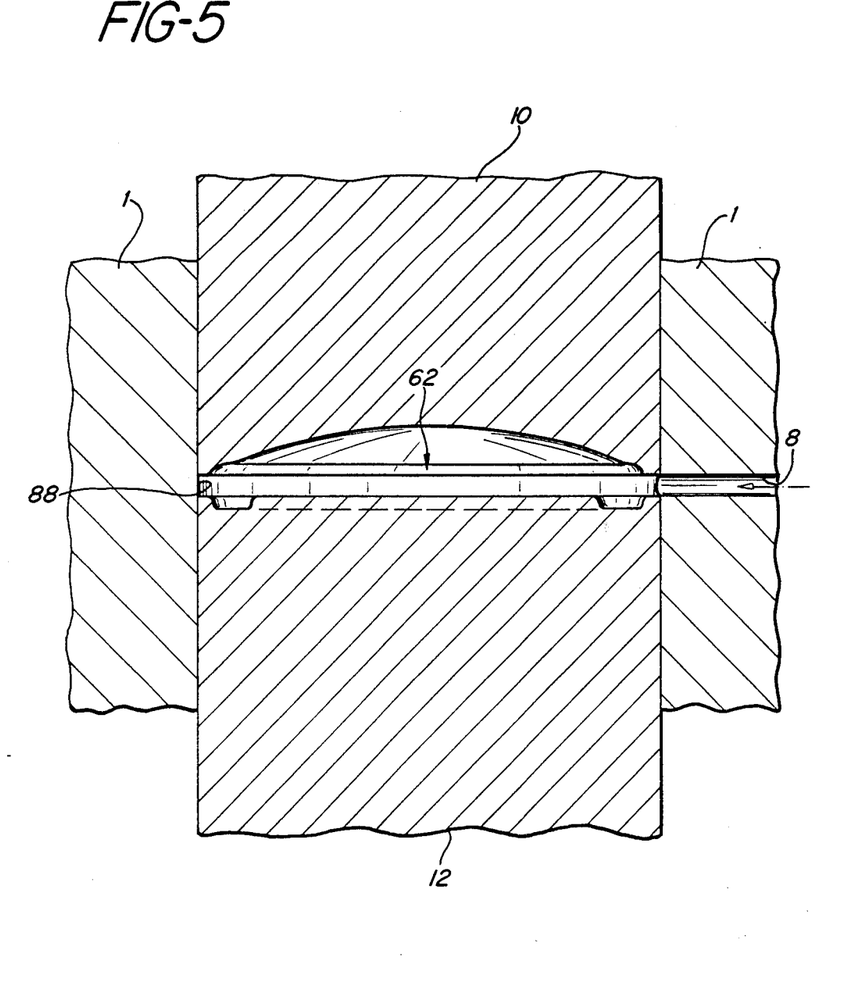
FIG. 5 shows a cross-sectional view taken along the line 5—5 in FIG. 4 showing the mold cavity provided by the present invention.

Referring now to FIG. 5, pins 10 and 12 are shown placed in mold insert 1 in their desired spaced apart relationship to form molding cavity 62, which can be filled with molten plastic material to form the optic of the present invention.

Figure 6:
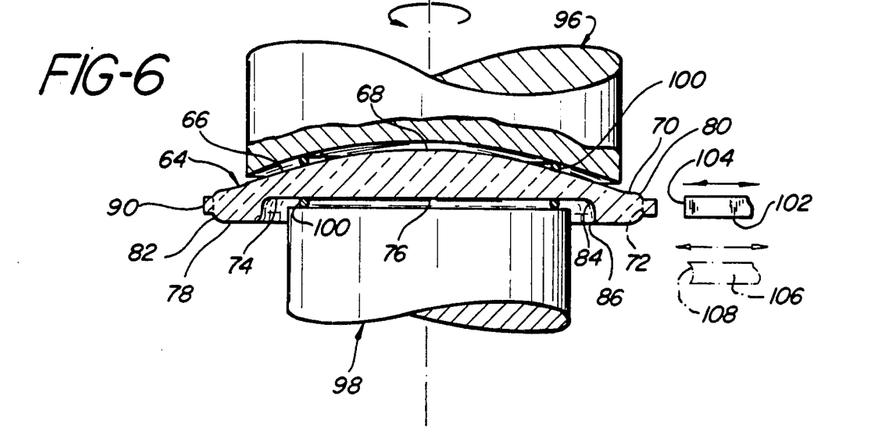
FIG. 6 shows the deflashing operation of the present invention.

Referring now to FIG. 6, there is shown the molded optic 64 as it appears when it is removed from mold cavity 62. Optic 64 has a convex anterior optical surface 66, with a central optical zone 68 and an integrally molded ring portion 70 extending from optical zone 68 to the peripheral edge 72 of optic 64. The posterior surface 74 of optic 64 has a central optical zone 76. Posterior surface 78 of ring portion 70, is spaced posteriorly apart from posterior surface 74 so that posterior surface 74 is recessed from posterior surface 78. The anterior edge 80 and posterior edge 82 of optic 64 include finished, molded radii which require only minimum additional finishing. Anterior recess edge 84 and posterior recess edge 86 are also molded, finished radii which require little or no additional finishing.

Referring again to the mold cavity shown in FIG. 5, it can be seen that the confronting flat surfaces 40 and 54, and the adjacent side wall of bore 6 of mold insert 1, provide a generally rectangular gate and flash area 88 for introducing plastic into mold cavity 62. When the optic 64 is removed from mold insert 1, the part of the optic formed in flash area 88 is designated as flash 90.

Figure 7:
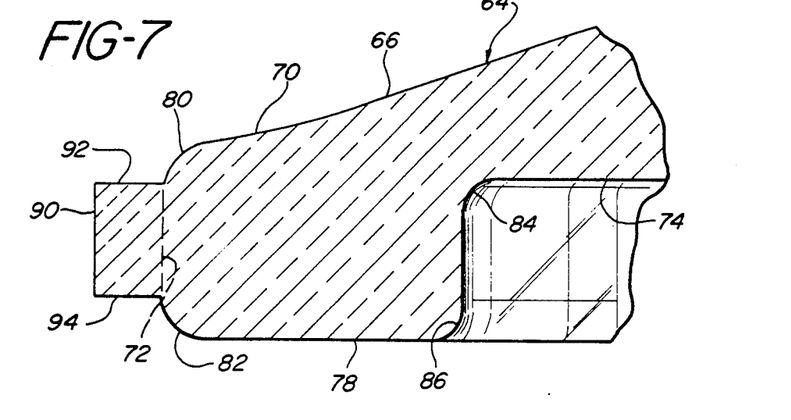
FIG. 7 shows a detail of the optic of the present invention before it is deflashed; and, FIG. 8 shows the finished optic of the present invention.

Referring now to FIG. 7, it can be seen that flash 90 is a generally annular ring extending about the periphery 72 of optic 64 and it has a generally rectangular cross-section. The anterior surface of 92 of flash 90 intersects periphery 72 of optic 64 at a point posteriorly of the radius on the anterior edge 80 of optic 64. Likewise, posterior surface 94 of flash 90 intersects periphery 72 at a point anterior of the radius of posterior edge 82. Flash 90 may be removed with a straight cutting tool so that the resulting peripheral edge 72 of optic 64 will blend smoothly with the adjacent radii on the anterior edge 80 and posterior edge 82 of optic 64. The cross-section of flash material 90 need not be rectangular. If flats 40 and 54 are not perpendicular to the axis of their respective pins 10 and 12, and they need not be, the flash material may have a trapezoidal or other four-sided shape. The large or small base of the trapezoid may be placed against peripheral edge 72 of optic 64.

Referring now to FIG. 6, there is shown the optic 64 as it appears when it is removed from mold insert 1. Optic 64 is placed between the confronting surfaces of mandrels 96 and 98. The optical surfaces of optic 64 are protected by O-rings 100, or some other suitable protector device to prevent mandrels 96 and 98 from damaging the optical surfaces of optic 64. Mandrels 96 and 98 rotate together at the same speed as shown in FIG. 6. A finishing tool 102, has a straight cutting edge 104 extending in the direction of the optical axis of optic 64 for a distance greater that the thickness of flash 90. Alternatively, cutter 106 may be used having an arcuate cutting surface 108 which blends with the radii of the adjacent anterior edge 80 and posterior edge 82 of optic 72 to provide a smooth, curved peripheral edge to optic 64. After flash 90 is removed, peripheral edge 72 of optic 64 may be subjected to light polishing, if necessary.

Thus, it can be seen that the present invention provides an optic 64 which has finished, molded radii at all of its edges which require only minimum post-molding, finishing or polishing. It is only necessary to deflash and degate the optic.

Figure 8:
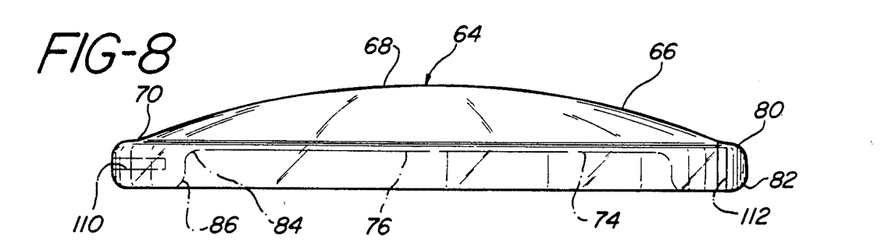

Referring now to FIG. 8, it can also be seen that optic 64 of the present invention has a thin central optical zone 68 which allows the lens to provide better optical properties. Optic 64 also has a reasonably thick annular peripheral ring 70 which is sufficiently thick to provide adequate support for haptic loops. Holes 110 may be drilled in the radial direction in the ring portion 70 to provide support for haptic loops. Positioning holes 112 may be drilled in ring portion 70 in a direction generally parallel to the optical axis of optic 64, to provide a means for maneuvering the optic after it has been inserted in the eye.

The recess provided in the posterior surface of optic 64 is useful for spacing the posterior optical surface 76 away from the capsular bag into which the optic may sometimes be inserted to provide space for a later capsulotomy, if necessary.

The present invention has been described in conjunction with preferred embodiments. Those skilled in the art will appreciate that many modifications and changes may be made to the preferred embodiments without departing from the scope of the present invention. It is, therefore, not intended to limit the present invention except as set forth in the appended claims.

What is claimed:

1. A mold for a thin, light weight, plastic optic for an intraocular lens comprising:
   I. A mold insert having a bore for receiving first and second molding pins in opposed relationship so that the confronting surfaces of said first and second molding pins and said bore define a molding cavity;
   II. A first molding pin adapted for insertion into said mold bore and which provides a substantially finished molded radius on the edge of the lens which edge needs no degating or deflashing after molding having:
      (a) a generally cylindrical body having a circumferential surface, having an axial length, and having a distal surface extending generally transversely to the axis of said body defining the anterior surface of said optic, said distal surface having a highly polished central portion defining an optical zone for said anterior surface of said optic, said distal surface including a peripheral portion extending from the edge of said optical zone to the circumference of said body;
      (b) said peripheral portion having an annular groove therein, the radially inward portion of which blends smoothly with the adjoining distal surface of said peripheral portion and said central optical zone;
      (c) the tangent to the radially outward edge of the groove, extending generally parallel to the axis of said body and said radially outward edge of said groove spaced apart from the circumference of said body a small distance;
      (d) a flat portion extending from the radially outwardly edge of said groove to the circumference of said body; and spaced axially from the surface of said peripheral zone said flat portion providing a space for flash material attached to the peripheral edge of said lens so that flash may be removed from the molded optic without changing the molded radius applied to the edge of said lens; and
      (e) said groove providing a molded radius on the edge of the anterior surface of said optic which edge needs no degating or deflashing after molding;
   III. A second molding pin which provides a substantially finished molded radius on the edge of the lens which edge needs no degating or deflashing after molding, adapted for insertion into said mold bore in opposed relationship to said first molding pin; said second molding pins including;
      (a) a generally cylindrical body having a circumferential surface, having an axial length and having a distal surface;
      (b) said distal surface of said body defining a posterior surface of said optic and including a highly polished central optical zone; and
      (c) said distal surface of said body including a peripheral portion extending from the edge of said body distal surface central optical zone to the circumference of said body.

2. The mold of claim 1 wherein said flat portion of said first molding pin is aligned generally perpendicular to the axis of said body.

3. The mold of claim 1 wherein said distal surface of said body of said first molding pin includes a generally concave central optical zone.

4. The mold of claim 1 wherein said second molding pin further includes on said body peripheral portion, an annular channel, having a base, a first wall and a second wall disposed radially outwardly of said first wall;

the intersection of said body distal surface and said first channel wall defining a smooth radius;

the intersection of said channel base and said first wall defining a smooth radius;

the intersection of said channel base and said channel second wall defining a smooth radius;

said second wall spaced inwardly from the circumference of said body, the portion of said distal surface between said second wall and said circumference of said body defining a flat area;

the intersection of said flat area and said second channel wall defining a sharp corner; and, said second wall having a height such that said flat area is spaced axially from the base of said channel, said flat area providing a space for flash material attached only to the peripheral edge of said lens so that flash may be removed from the molded optic without changing the molded radius applied to the edge of the lens.

5. The mold of claim 4 wherein said flat area of said second molding pin is aligned generally perpendicular to the axis of said body.

6. The mold according to claim 4 wherein said distal surface of said body of said second molding pin includes a generally planar central optical zone, disposed perpendicular to the axis of said body.

* * * * *